(12) United States Patent  (10) Patent No.: US 8,734,734 B2
Kido et al.  (45) Date of Patent: May 27, 2014

(54) LIQUID ANALYSIS CARTRIDGE

(75) Inventors: Horacio Kido, Lake Forest, CA (US);
Jim Norton, Santa Ana, CA (US);
James W. Egan, Jr., Lynch, MD (US)

(73) Assignee: LaMotte Chemical Products Company, Chestertown, MD (US)

( * ) Notice: Subject to any disclaimer, the term of this patent is extended or adjusted under 35 U.S.C. 154(b) by 0 days.

(21) Appl. No.: 13/611,843

(22) Filed: Sep. 12, 2012

(65) Prior Publication Data

US 2014/0072474 A1  Mar. 13, 2014

(51) Int. Cl.
*B01L 3/00*  (2006.01)
*B01F 13/00*  (2006.01)

(52) U.S. Cl.
CPC ....... *B01L 3/5027* (2013.01); *B01F 13/0059* (2013.01); *B01L 2300/0829* (2013.01); *B01L 2300/0867* (2013.01); *B01L 2400/0409* (2013.01)
USPC .......................................... 422/506; 422/502

(58) Field of Classification Search
CPC .................... B01L 2300/819; B01L 2300/829; B01L 2300/0803; B01L 2300/0861; B01L 2300/0867; B01L 2300/087; B01L 2400/0409
USPC ................................................ 422/502, 506
See application file for complete search history.

(56) References Cited

U.S. PATENT DOCUMENTS

| | | | |
|---|---|---|---|
| 3,795,451 A | 3/1974 | Mailen | |
| 5,304,348 A | 4/1994 | Burd et al. | |
| 5,591,643 A | 1/1997 | Schembri | |
| 6,342,395 B1 | 1/2002 | Hammock et al. | |
| 6,395,562 B1 | 5/2002 | Hammock et al. | |
| 6,752,961 B2 | 6/2004 | Kopf-Sill et al. | |
| 6,965,433 B2 | 11/2005 | Zoval et al. | |
| 7,889,615 B2 | 2/2011 | Worthington et al. | |
| 8,043,562 B2 | 10/2011 | Tomasso et al. | |
| 2002/0145960 A1 | 10/2002 | Worthington et al. | |
| 2003/0077627 A1 | 4/2003 | Worthington et al. | |
| 2004/0226348 A1 | 11/2004 | Bruce, III et al. | |
| 2004/0230400 A1 | 11/2004 | Tomasso et al. | |
| 2005/0084422 A1 | 4/2005 | Kido et al. | |
| 2005/0170490 A1 | 8/2005 | Chen et al. | |
| 2005/0221048 A1 | 10/2005 | Norton et al. | |
| 2007/0077173 A1 | 4/2007 | Melet | |
| 2007/0125942 A1 | 6/2007 | Kido | |
| 2008/0101993 A1 | 5/2008 | Andersson et al. | |
| 2008/0110500 A1 | 5/2008 | Kido et al. | |
| 2008/0190503 A1 | 8/2008 | Zoval et al. | |
| 2008/0286156 A1 | 11/2008 | Andersson et al. | |
| 2008/0317634 A1 | 12/2008 | Kido et al. | |
| 2009/0120504 A1 | 5/2009 | Andersson et al. | |
| 2011/0094600 A1 | 4/2011 | Bergeron et al. | |
| 2011/0111987 A1 | 5/2011 | Siegrist et al. | |

*Primary Examiner* — Lyle Alexander
(74) *Attorney, Agent, or Firm* — Drinker Biddle & Reath LLP

(57) ABSTRACT

An analytical cartridge and a rotary analytical device with which the cartridge cooperates. The cartridge may have a housing, an axis, analysis chambers spaced from and located circumferentially about the axis, and a magnetically movable element located in and movable within each analysis chamber to mix fluid in the analysis chamber. The rotary analytical device may have a housing with a cavity having an axis, an impeller extending into the cavity and rotatable about the axis to receive and rotate the cartridge, a motor to rotate the impeller, at least one magnetic element near the cavity and offset from the axis, a light source in the housing to direct a beam of light into the cavity and through the analysis chamber of the cartridge, and a light sensor to receive light from the analysis chamber.

16 Claims, 5 Drawing Sheets

LIQUID ANALYSIS CARTRIDGE

BACKGROUND OF THE INVENTION

It is frequently desired to analyze is liquid to determine the presence and concentration of analytes such as minor constituents and/or contaminants. In many instances, several different tests may be run on one or more portions of a single liquid sample, to detect and measure different constituents. For man common tests, reagents are available that provide an almost instantaneous result by changing either hue or intensity of color in response to a specific constituent in the liquid. An example is a swimming-pool test kit, which typically provides from two to six different reagents that test for common factors such as chlorine or bromine content, pH, and hardness of the water.

However, such test kits conventionally require the user to fill a specific amount of water into a test container, add a specific amount of reagent, judge the intensity or hue of the resulting color against a reference chart by eye, and repeat the whole process for each test that it is desired to carry out, if the test results are not within is desired range, the user must then manually calculate the amounts of chemicals to add to the swimming pool to adjust its condition to the desired range. That is time consuming, messy, and not very accurate. The situation is even worse for a pool supply store, where the store staff are frequently asked for assistance by a pool owner whose pool chemistry has gone wrong in a way that the owner cannot himself correct. The store staff may then need to conduct a much larger range of tests, and to convert the results of the tests to quantities of various chemicals to be added to the pool.

Similar issues occur in other businesses and industries. For example, in brewing, trace constituents of the water used can not only directly affect the flavor and quality of the brewed beverage, but also affect the behavior of the yeast and therefore the success and result of the brewing process. Other businesses in which a battery of tests, have to be performed fairly frequently, so that similar issues occur, include aquaria, aquaculture, environmental monitoring, and maintaining boilers and coolers.

There is, therefore, a need for apparatus and methods that make it possible to test a liquid sample for several different properties, for example, for the presence or absence of several different analytes, in a single operation, with a minimum of mess, and to obtain the results of the tests automatically, without relying on human judgment.

SUMMARY OF THE INVENTION

One embodiment of the invention provides an analytical cartridge comprising a cartridge housing, having a central axis, a plurality of analysis chambers in the housing, the chambers being spaced apart from the axis and located circumferentially about the axis, and a magnetically movable element located in each analysis chamber and movable within the analysis chamber, the element adapted to cause the mixing of fluid in the analysis chamber.

Another embodiment of the invention provides a rotary analytical device comprising a housing having a cavity formed therein, the cavity being defined by a bottom wall and at least one side wall, the cavity having an axis, an impeller extending into the cavity and rotatable about the axis a motor mounted within the housing and connected to the impeller, the motor adapted to rotate the impeller, at least one magnetic element in the housing at a location proximate to the cavity and offset from the axis, at least one light source in the housing and arranged to direct a beam of light into the cavity, and at least one light sensor in the housing and arranged to receive light from the at least one light source, the sensor being sensitive to light of a color emitted by the light source.

Further embodiments of the invention provide combinations of a rotary analytical device and an analytical cartridge co-operating with the rotary analytical device, and methods of analysis using such rotary analytical devices, such analytical cartridges, and such combinations of a rotary analytical device and an analytical cartridge.

BRIEF DESCRIPTION OF THE DRAWINGS

The above and other aspects, features, and advantages of the present invention may be more apparent from the following more particular description of embodiments thereof, presented in conjunction with the following drawings. In the drawings.

DETAILED DESCRIPTION OF THE PREFERRED EMBODIMENTS

A better understanding of various features and advantages of the present methods and devices may be obtained by reference to the following detailed description of illustrative embodiments of the invention and accompanying drawings. Although these drawings depict embodiments of the contemplated methods and devices, they should not be construed as foreclosing alternative or equivalent embodiments apparent to those of ordinary skill in the subject art.

Figure 1:
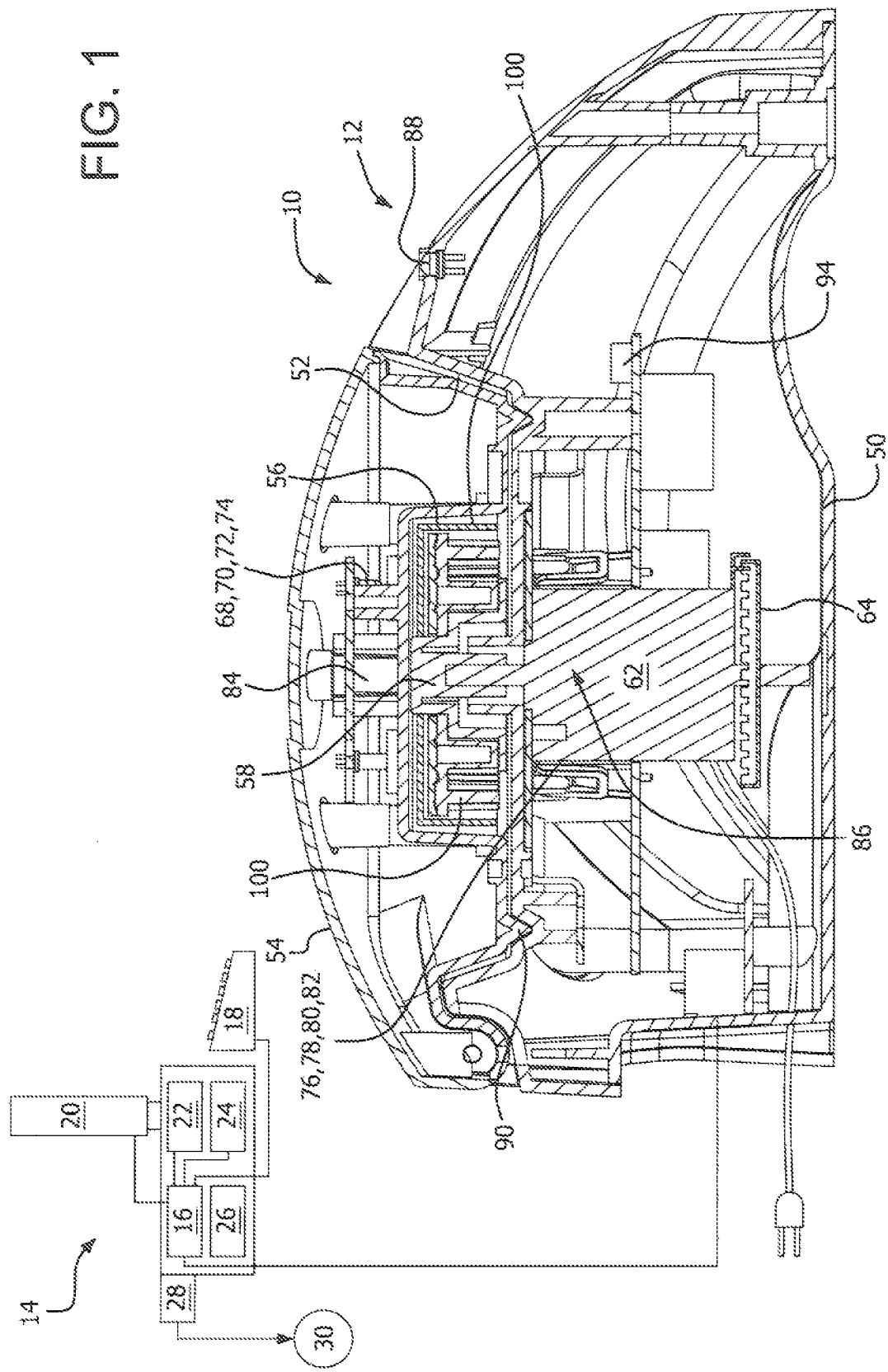
FIG. 1 is a schematic view of an embodiment of a liquid analysis apparatus.
Figure 2:
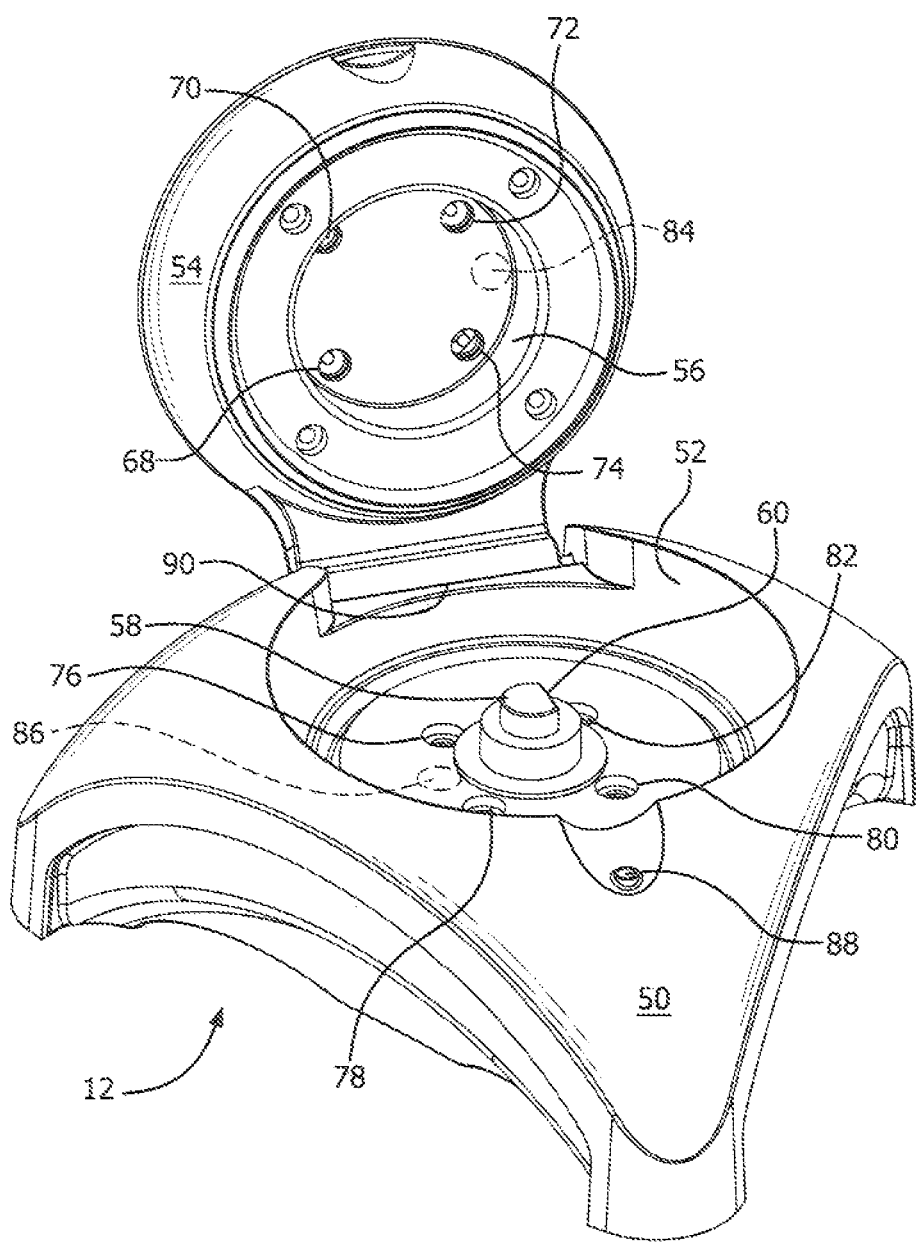
FIG. 2 is as perspective view of a rotary analyzer forming part of the liquid analysis apparatus of FIG. 1.

Referring to the drawings, and initially to FIG. 1, one form of liquid analysis apparatus, indicated generally by the reference number 10, comprises a rotary analyzer, indicated generally by the reference number 12 and shown in more detail in FIG. 2, connected to a computer 14. Computer 14 may be a conventional personal computer or similar device suitably programmed, and may comprise, among other equipment, a processor or controller 16, input and output devices such as a keyboard 18 and a monitor 20, random access memory (RAM) 22, read-only memory (ROM) 24, magnetic disks or other long-term storage 26, and an interface 28 to an external network 10 or other communications media. The interface 28 may also provide a connection from the computer 14 to the rotary analyzer 12.

Referring, now also to FIG. 2, the rotary analyzer 12 comprises a base 50 defining a recess 52 in its upper surface, and a lid 54 hinged to base 50 and defining a generally cylindrical recess 56 in its lower surface. When the lid 54 is closed, it preferably fits into recess 52. A spindle 58 projects through the lower surface of the recess 52 and is received in the recess 56 when the lid 54 is closed. The spindle 58 has a flat surface 60 on one side. Below the bottom of the recess 52, the spindle 58 is connected to and driven by a motor 62, and is preferably connected to a rotary encoder 64 or similar device by which its rotational position can be monitored. However, as will become apparent after review of the following description, other well known mechanisms can be used to provide rotational position signals to the apparatus.

In the embodiment shown, four light sources, preferably light emitting diodes (LEDs) 68, 70, 72, 74 are mounted in the underside of the lid 54 in the top of recess 56. The LEDs 68, 70, 72, 74 may be of different colors, for example, respectively red, yellow, green, and blue. Four light detectors, such as phowdiodes or other photoelectric transducers 76, 78, 80, 82, are mounted in the bottom of the recess 52, each facing a respective one of LEDs 68, 70, 72, 74. Each transducer 76, 78, 80, 82 may be provided with a dichroic or other band-pass filter or otherwise optimized to be selectively sensitive to the light from its respective LED. It is also contemplated that the light sources could be located on the same side as the detectors (e.g., the bottom of the recess) with a reflective surface mounted on the opposite side of the recess (e.g., on the lid).

In other embodiments, more or fewer light sources, and/or light sources of different colors, which may include infrared and/or ultraviolet, may be used. In other embodiments, other sorts of light sources, which may include a broadband source such as an incandescent lamp, may be used.

A first permanent magnet 84 is mounted in the underside of lid 54 between two of the LEDs. A second permanent magnet 86 is preferably mounted in the bottom of recess 52, between two of the transducers, spaced apart from the first magnet 84. The LEDs 68, 70, 72, 74, the transducers 76, 78, 80, 82, and the magnets 84, 86 are preferably all at the same radius from the axis of rotation of spindle 58, however it is contemplated that the magnets can be located to a different radius depending on the construction of the cartridge.

An indicator lamp 88 may be provided on the exterior of the rotary analyzer 14, in a position where it is easily visible even with lid 54 dosed. An interlock switch 90 may be provided to detect when lid 54 is closed.

A processor or controller 94 suitably programmed is provided, and receives inputs from the transducers 76, 78, 80, 82, the rotary encoder 64, and interlock switch 90, and controls the LEDs 68, 70, 72, 74, the motor 62, and the indicator light 88. The interlock switch 90 is preferably configured to provide signal to the processor or controller 94 for detecting when the lid is closed in order to prevent activation of the spindle 58 when the lid is not in its closed position. The indicator light 88 preferably is illuminated when the analyzer is active or when the testing is complete.

Figure 3:
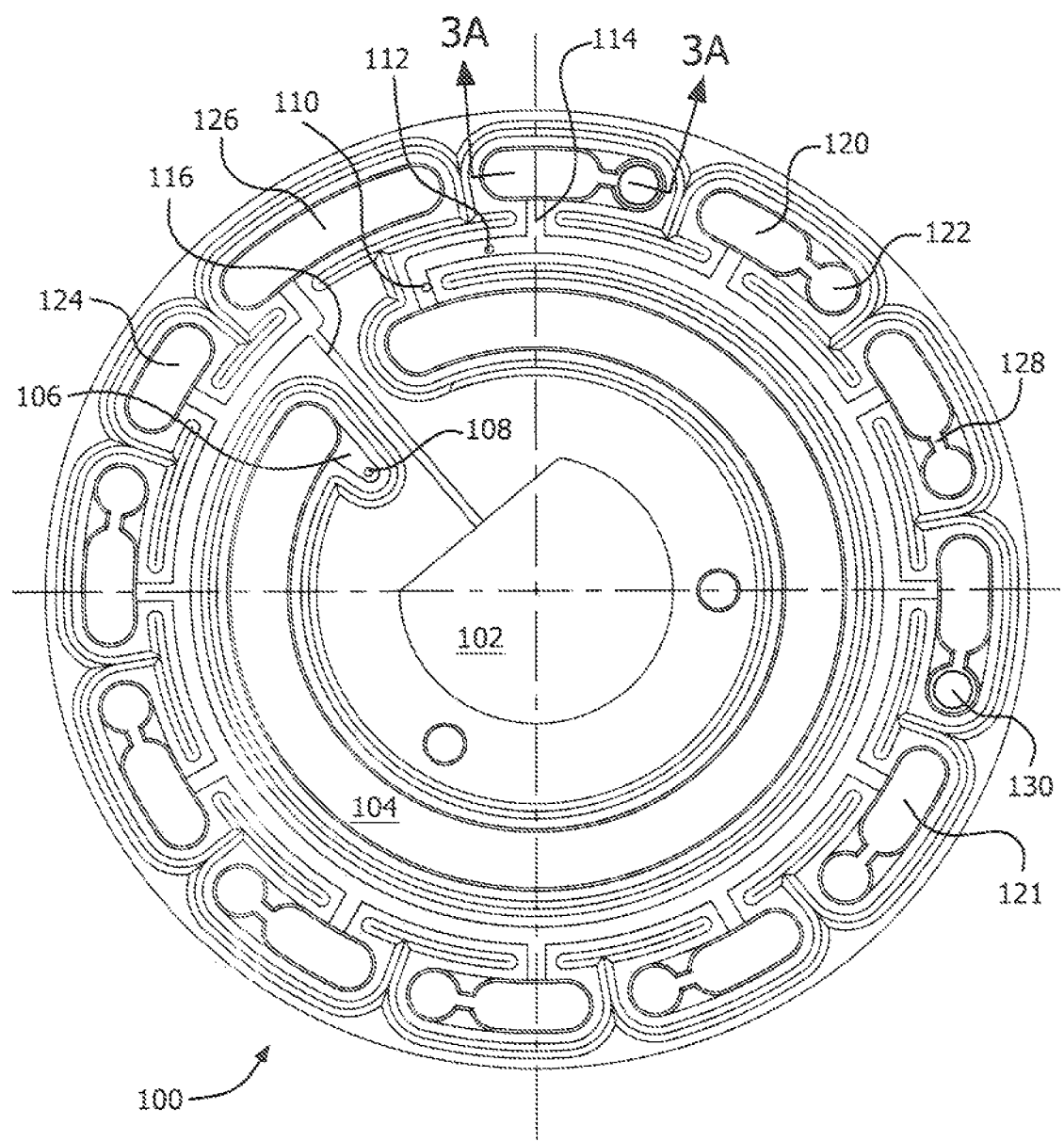
FIG. 3 is a top plan view of a cartridge used in the rotary analyzer of FIG. 2.

Referring now also to FIG. 3, one form of cartridge, indicated generally by the reference number 100, comprises a molded body with a generally flat lid or top surface 101. Cartridge 100 comprises a central opening 102 that is preferably D-shaped an configured to engage with the flat 60 on the spindle 58, so that when the cartridge 100 is mounted on the spindle 58 the orientation of the cartridge 100 relative to the rotary encoder 64 is fixed and predetermined. It is contemplated that the opening 102 can be any suitable non-circular shape designed to mate with a complementary spindle shape.

At least partially surrounding the central opening 102 is an annular filling chamber 104, which in one embodiment extends around the opening about 330° of the circumference of the cartridge. At one end of the filling chamber 104 preferably includes a radially inward extension 106, that includes a filling port 108, which is the an opening through the lid of cartridge 100.

Water can be injected through filling port 108 using a conventional syringe (not shown) into filling chamber 104. Visible indicia may be molded into or placed on the lid of the cartridge 100, for example, to point out where the filling port 108 is located and/or to indicate a point to which the filling chamber 104 should be filled.

At the end of the filling chamber 104 remote from the filling port 108, a transfer passage 110 extends radially outward to a distribution gallery 112, which in the illustrated embodiment almost completely encircles the cartridge 100 outside the filling chamber 100. Of course it is contemplated that multiple passages 100 can communicate with multiple galleys 112. From the distribution gallery 112, a plurality of spouts or channels 114 extend radially outward. From the end of the distribution gallery 112 furthest from the transfer passage 110, there is preferably located an overflow passage 116 that extends radially inwards, and opens into the central opening 102 through the flat side of the D-shaped opening.

Outside the distribution gallery 112 are several analysis chambers 120, each with an associated agitator chamber 122, at least one comparison chamber 124, and an overflow chamber 126. The analysis chambers 120, comparison chamber 124 and overflow chamber 126 are each connected to the distribution galley through one of the channels 114. The analysis chambers 120 are located circumferentially on a circle with a radius that corresponds to the radial location of the LEDs 68, 70, 72, 74, the photoelectric transducers 76, 78, 80, 82, and preferably the magnets 84, 86. The analysis chambers 120 are preferably equally sized and evenly spaced, although that is not necessary in the present invention. In the cartridge 100 shown in FIG. 3, there are ten analysis chambers 120, spaced at intervals of approximately 30° (1/12 of the circumference of the cartridge). The comparison chamber 124 occupies an eleventh position, and in the illustrated embodiment is about the same size as an analysis chamber, but does not have an associated agitator chamber. The overflow chamber 126 occupies the twelfth position, and is larger than the analysis chambers. The overflow chamber 126 uses up the space that is available where the overflow and comparison chambers do not have agitator chambers. The overflow chamber 126 is at the same end of distribution gallery 112 as the overflow passage 116.

Figure 3A:
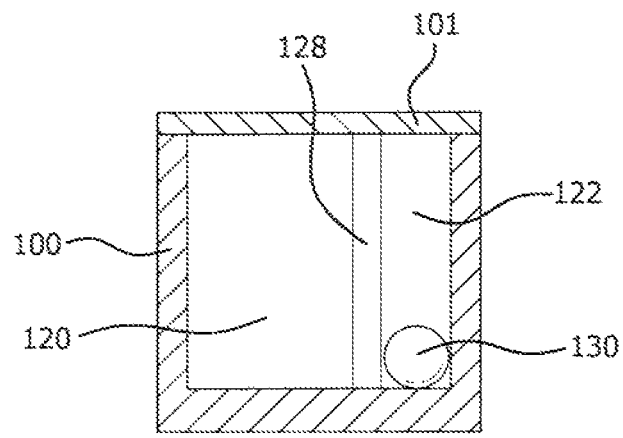
FIG. 3A is a cross-section view of an analysis chamber and agitator chamber.
Figure 3B:
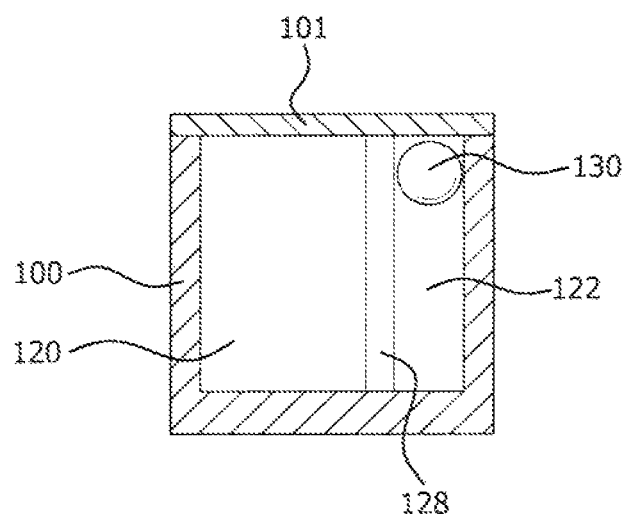
FIG. 3B is a view similar to FIG. 3A in a different position in operation.

As shown in FIG. 3A, the analysis chambers 120 are elongated in the circumferential direction, and extend between the top and bottom of the cartridge 100, dosed off by the lid 101. The agitator chambers 122 are preferably generally circular in cross-section, and extend between the top and bottom of the cartridge 100, closed off by the lid 101. Each agitator chamber 122 is connected to its associated analysis chamber 120 by a slot 128 preferably extending between the top and bottom of the cartridge. Each agitator chamber 122 contains an agitator 130 preferably in the form of a magnetizable stainless steel ball bearing (BB) that is small enough to move freely along the agitator chamber 122 between the positions shown in FIG. 3A and FIG. 3B, but large enough to displace water like a piston when it does so, and too large to pass through the slot 128.

The top and bottom faces or surfaces of the cartridge 100 above and below the analysis chambers 120 are preferably made smooth, flat, and clear, so as to permit the transmission of light with minimal absorption and scattering.

In a ready-for-use condition of the cartridge 100, each analysis chamber 120 contains a predetermined amount of a selected reagent 121. Preferably, the reagents 121 are introduced into the analysis chambers 120 in liquid form and dried or allowed to dry onto the bottoms of the analysis chambers, thus immobilizing the reagents so that they do not move outside their respective chambers during shipping. Alternatively, the reagents could be dried prior and then metered into the chambers. Once the reagents and the agitators 130 have been introduced into the cartridge 100, the lid 101 is attached, for example, by sonic welding. In one example of a cartridge for analyzing swimming-pool water, the reagents are suitable for measuring one or more of the following, preferably all: free chlorine/bromine; total chlorine; total alkalinity; pH; calcium and/or magnesium hardness (at two different ranges); copper; iron; borate; and cyanuric acid. In another example, biguanide and biguanide shock measuring reagents are substituted for the chlorine and bromine tests, and the cyanuric acid test is omitted.

In use, a measured amount of water or other liquid to be analyzed is injected into the filling chamber 104 through the filling port 108. The amount may be measured by tilling the filling chamber 104 until the water reaches a visible filling mark, for example, until the boundary between the area of the chamber 104 furthest from the fill port 108 is filled and at a location underneath or between lines molded on the cartridge 100. As liquid is injected in the filling chamber 104, air in the chamber is displaced through the overflow passage 116. Other mechanisms for venting air can be provided, such as a vent port on the distribution gallery 112. The cartridge 100 is then placed over the spindle 58, with the flat surface 60 on the spindle 58 engaging the flat side of D-shaped opening 102 in the cartridge 100.

A cover 140 is then preferably placed over cartridge 100. The cover 140 may be made from an opaque or black material or suitably coated to limit and absorb stray light from the LEDs 68, 70, 72, 74, and may be made of a strong plastic to protect the analyzer 12 if there is any failure of the cartridge 100. The cover 140 may have openings aligned with the analysis chambers 120, and a D-shaped central opening that engages the flat 60 of spindle 58 so that the openings in the cover 140 remain in alignment with the analysis chambers 120. The cover 140 may be omitted. In an alternative embodiment, another provision may be made for reducing stray light. For example, the spindle 58 may be provided with a fat plate on which the cartridge 100 rests, and which has openings aligned with the analysis chambers 120.

Once the cartridge is mounted, the lid 54 is closed, and the analyzer 12 is activated, either by a control on the analyzer itself or by a command signal from a computer 14. The motor 62 rotates the spindle 58, which rotates the cartridge 100 at a speed suitable for generating sufficient centrifugal force to cause the liquid to flow outward from the filling chamber 104 through the transfer passage 110 to the distribution gallery 112. The liquid flows along the distribution gallery 112, and outward, again by centrifugal three through the channels 114 to fill the analysis chambers 120 and the comparison chamber 124. Any excess liquid will pass through the whole length of the distribution gallery 112 into the overflow chamber 125. Any excess liquid should remain in filling, chamber 104 or distribution galley 112, because the outlet of overflow passage 116 is radially inward from the distribution galley, closer to the center of rotation.

Once the liquid has been distributed to the analysis chambers 120, the motor 62 continues to rotate the cartridge 100. As each agitator chamber 122 passes the magnets 84, 86, the agitator 130 is attracted by the magnets and moves alternately up and down within the agitator chamber 122, between the positions shown in FIGS. 3A and 313, depending on the magnet it passes. The movement of the agitator 130 causes an oscillating circulation of liquid within the agitator chamber 122 and its associated analysis chamber 120. The circulation of liquid assists in the dissolving or suspension of the reagent 121 into the liquid, and facilitate the even mixing of the reagent 121 throughout the liquid in analysis chamber 120.

Each reagent is preferably formulated using known techniques such that it forms an appearance such as hue, intensity of color, or opacity that is detectable or measurable by light, depending on the presence, absence, or concentration of the analyte that each reagent is intended to detect. In an embodiment, different reagents 121 in the different analysis chambers 120 from different colors, depending on the concentration of the analyte that each reagent is intended to detect.

Each color may be measured by the absorption of the light from one or more of the LEDs 68, 70, 72, 74 before it reaches its respective transducer 76, 78, 80, 82, or alternatively, by the amount of light that passes through to the respective transducer. The colors may vary in hue, intensity, or both. For example, one standard reagent for measuring chlorine concentration produces a pink color that becomes darker as the chlorine concentration increases, and may be measured by the absorption of blue light from the LED 74. For example, one standard reagent for measuring pH varies in hue from yellow at low pH to red at high pH, and may be measured by the absorption of light from the yellow LED 70 or the green LED 72. A reagent that varies it hue may also be measured by the difference between absorptions of light from light sources of two different colors.

Errors caused by variation in the intensity of the light emitted by the LEDs, and lack of transparency of the initial liquid samples, may be corrected by measuring the light transmitted through the reference chamber 124. The light of each color transmitted by each chamber may be identified by synchronizing the time-varying output from the transducers 76, 78, 80, 82 with the timing information from the rotary encoder 64 as the spindle 58 rotates.

In an embodiment, the processor 94 repeatedly samples the measured light intensity data from the transducers 76, 78, 80, 82. The processor 94 discards readings that do not match one of the analysis chambers 120 or the reference chamber 124. Merely by way of example, the processor 94 may sample the transducers 400 times per revolution of the cartridge 100, and extract 4 readings for each analysis chamber 120 per revolution. The readings are then averaged over several revolutions, and a matrix of 11×4 averaged readings is transmitted by the processor 94 to the computer 14. The computer 14 is programmed with calibration data for the set of reagents 121 in the cartridge 100, and converts the light intensity data into concentrations of the various analytes. Programs for converting the light intensities into analyte concentrations, including databases of the characteristics of standard reagents, are commercially available and, in the interests of conciseness, need not be further described here. The computer 14 may display the concentrations on screen 20. While the analyzer is shown having a processor 94 mounted within it, it is also contemplated that all the processing may occur at the computer. Alternatively, the processor 94 can be programmed to provide all the analysis necessary and provide the results to the computer or other display device.

Instead, or in addition, where the liquid sample being analyzed has a desired or ideal condition (as is the case, for example, with swimming pool water) the computer 14 may be programmed with a data file of available treatments to adjust the condition. Optionally, relevant properties of a source of the liquid sample being analyzed may also be stored on the computer 14 or input during the analysis, and the computer 14 may then generate a prescription for treatments to correct any problem detected by the analysis.

For example, if the sample being analyzed is water from a swimming pool being analyzed at a pool supplies store, one important piece of information, is the size of the pool. If the analysis shows that the water is outside a desirable range for one or more analytes in the specific size pool, the computer 14 can then generate a list of specific quantities of select pool chemicals that are in stock in the store and needed to correct the results of the analysis. Because different brands of chemicals may come in different formulations, container sizes, and concentrations, that typically may require at least a separate data file for each brand.

As an example of suitable dimensions, for a water analyzing apparatus for swimming-pool water, a cartridge as shown in FIG. 3 may be approximately 23 mm (15/16 inch) in radius to the centers of the analysis chambers, and approximately 12 mm (½ inch) high. The amount of water used may be from 2.7 to 2.9 ml. The cartridge may be rotated at around 2300 rpm to distribute the water to the analysis chambers 120 and the reference chamber 124 and to expel bubbles, and then at a maximum of 4500 rpm to ensure proper transfer of the water from the filling chamber to the reaction chambers, and at 300 rpm to obtain the optimum pumping action from the agitators. The rotation is continued for a period sufficient to allow the reagents to become dissolved in the water, to react with their respective analytes, and for the color or other measurable optical property to develop. It is presently believed that an analysis of swimming pool water of acceptable quality can be obtained in less than a minute from when rotation starts.

It is contemplated that the cartridge my include indicia, such as a bar code, RFID tag, or other form of information that can be read, such as with a scanner or reader mounted in the analyzer, which determines the reagents that are stored in the cartridge being analyzed. This permits an analyzer to be used with multiple cartridges, without the user having to input anything. However, it is also contemplated that the user can select the sample being analyzed (e.g., pool water, water for beer brewing process, etc.) directly on the computer. The computer would use the information for purposes of selecting the appropriate data file for analyzing the sample data transmitted from the analyzer.

Figure 4:
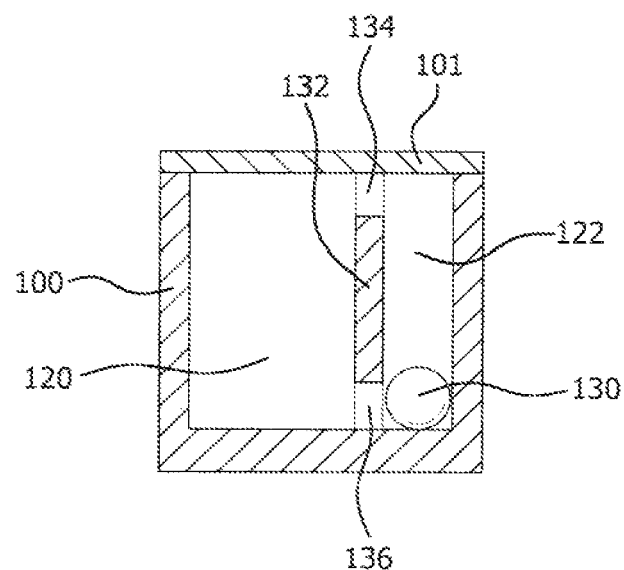
FIG. 4 is a view similar to FIG. 3A of an alternative embodiment.

Referring now also to FIG. 4, an alternative embodiment of the cartridge 100' is similar to that described above except that, in place of slot 128, the analysis chamber 120 and the agitator chamber 122 are separated by a solid septum 132, with apertures 134, 136, at both ends. The cartridge 100' may be used in the same way as the cartridge 100. In use, movement of agitator 130 up and down within agitator chamber 122 causes liquid to flow in and out through apertures 134, 136 alternately, resulting in a reciprocating flow within analysis chamber 120. The reciprocating flow causes turbulence within the analysis chamber 120 that assists in dissolution and distribution of the reagent.

Although specific embodiments have been described, various modifications are possible without departing from the spirit of the invention or the scope of the appended claims, and features of the different embodiments may be combined into one embodiment.

For example, although the agitators have been described as stainless steel ball bearings that are attracted to the magnets 84, 86, the agitators could instead also be magnets. If the agitators are elongated so that they cannot rotate within their chambers, they could be magnetically polarized so as to be repelled, instead of attracted, by one or more of magnets 84, 86. It is presently preferred to provide two magnets 84 and 86, so that agitators are positively driven both up and down once per revolution. However, more magnets could be provided, or in some circumstances there could be only a single magnet driving the agitators upwards, with the agitators being, returned by gravity.

In the cartridges 100, 100' shown in the drawings, the analysis chambers 120 and the reference chamber 122 are evenly spaced in a circle around the circumference of the cartridge. Other arrangements are possible. For example, there could be two concentric circles of analysis chambers.

The cartridge shown in FIG. 3 is intended to be disposable, and may be fabricated by gluing or welding a generally fiat lid on a molded body. However, the cartridge could instead be reusable, in which case the lid may be removable to permit cleaning and recharging of the reagents in the analysis chambers.

It would be possible to omit the rotary encoder 64, and use the signal from one or more of the LEDs and transducer pairs to provide a rotary encoder input to the processor 94. However, because the reagents in the analysis chambers 120 will cause the signals from the transducers 76, 78, 80, 82 to vary, a dedicated encoder 64 may give more reliable, and more easily interpreted signals.

As shown in the drawings, the LEDs 68, 70, 72, 74, the photoelectric transducers 76, 78, 80, 82, the magnets 84, 86, the cartridge analysis chambers 120, the cartridge agitator chambers 112, and the cartridge reference chamber 124 are all centered on a single rotational cylindrical surface centered on the axis of spindle 58. Other arrangements are possible. For example the magnets and agitators could be on one cylinder, and the LEDs, analysis and reference chambers, and transducers could be on another cylinder of different radius. One or both of those cylindrical surfaces could instead be conical. The magnets 84, 86 do not need to be exactly aligned with the agitator chambers 122, provided they are near enough to produce the desired motion of the agitators 130.

While the analyzer is shown having a processor 94 mounted within it, it is also contemplated that all the processing may occur at the computer. Alternatively, the processor 94 can be programmed to provide all the analysis necessary and provide the results to the computer or other display device.

Furthermore, while the figures show the analyzer connected directly to the computer, it is contemplated that the connection could be through an interact connection, thus permitting samples to be run in the analyzer at a location that is remote from the computer than analyzes the data and provides the results.

Accordingly, reference should be made to the appended claims, rather than to the foregoing specification, as indicating the scope of the invention.

The invention claimed is:

1. An analytical cartridge comprising:
 a cartridge housing having a central axis;
 a plurality of analysis chambers in the housing, the chambers being spaced apart from the axis and located circumferentially about the axis; and
 each analysis chamber including:
  an elongated first chamber section containing a magnetically movable element located in and movable along the first chamber section between a first end and a second end; and
  a second chamber section fluidly connected with the first chamber section at both ends of the first chamber section, wherein the fluid connection between the first and second chamber sections includes an axial slot that is narrower than a minimum dimension of the magnetically movable element;
 wherein movement of the magnetically movable element along the analysis chamber first section being operative to cause circulation of fluid between the first and second sections and mixing of fluid in the analysis chamber second section.

2. The analytical cartridge of claim 1, wherein a longest dimension of the first chamber section is an axial dimension parallel to said central axis, and wherein the fluid connection between the first and second chamber sections includes an axial slot that extends completely between the ends of the first chamber section.

3. The analytical cartridge of claim 1, wherein the analysis chamber contains a photometric reagent, and wherein the housing above and below the second chamber section includes a portion that is transparent to light of at least one wavelength appropriate for photometry of the reagent.

4. The analytical cartridge of claim 3, further comprising at least one reference chamber without a magnetically movable element.

5. The analytical cartridge of claim 3, comprising a distribution gallery located radially inward from and fluidly connected to the analysis chambers, the distribution gallery adapted to distribute a liquid to be analyzed to the analysis chambers through centrifugal force upon rotation of the cartridge about the axis.

6. The analytical cartridge of claim 5, wherein the distribution gallery has an inlet for receiving the liquid to be analyzed at one end, and is connected to an overflow chamber at the other end; and wherein the fluid connection with the analysis chambers includes a plurality of channels located between the inlet and the overflow chamber and extending radially from the distribution gallery, each channel connected to an analysis chamber.

7. The analytical cartridge of claim 4 wherein the analysis chambers and the at least one reference chamber are evenly spaced circumferentially about the axis, wherein the at least one reference chamber does not have a first chamber section, and wherein the overflow chamber is larger than one of the analysis chambers, and the overflow chamber and the at least one reference chamber together occupy the same space as two said analysis chambers.

8. The analytical cartridge of claim 3, wherein the magnetically movable element is a ball bearing.

9. An analytical cartridge comprising:
a cartridge housing having a central axis;
a plurality of analysis chambers in the housing, the chambers being spaced apart from the axis and located circumferentially about the axis, each analysis chamber including a first chamber section containing a magnetically movable element located in and movable within the first chamber section between first and second ends, the element adapted to cause the mixing of fluid in the analysis chamber, and a second chamber section fluidly connected with the first chamber section at both ends of the first chamber section, and wherein the fluid connection between the first and second chamber sections includes an axial slot that is narrower than a minimum dimension of the magnetically movable element;
at least one reference chamber in the housing, the reference chamber not including a magnetically movable element; and
a distribution gallery located radially inward from and fluidly connected to the analysis chambers, the distribution gallery adapted to distribute a liquid to be analyzed to the analysis chambers through centrifugal force upon rotation of the cartridge about the axis.

10. The analytical cartridge of claim 9, wherein the distribution gallery has an inlet for receiving the liquid to be analyzed at one end, and is connected to an overflow chamber at the other end; and wherein the fluid connection with the analysis chambers includes a plurality of channels located between the inlet and the overflow chamber and extending radially from the distribution gallery, each channel connected to an analysis chamber.

11. The analytical cartridge of claim 9 wherein the analysis chambers and the at least one reference chamber are evenly spaced circumferentially about the axis, wherein the at least one reference chamber does not have a first chamber section, and wherein the overflow chamber is larger than one of the analysis chambers, and the overflow chamber and the at least one reference chamber together occupy the same space as two said analysis chambers.

12. The analytical cartridge of claim 9, wherein the magnetically movable element is a ball bearing.

13. An analytical cartridge for a centrifugal analyzer, the cartridge comprising:
a substantially cylindrical cartridge housing having a central axis;
a plurality of analysis chambers in the housing, the analysis chambers being spaced radially outward from and circumferentially about the axis, each analysis chamber including an agitator section containing a magnetically movable agitator that is movable within the agitator section between a first end and a second end, the agitator adapted to cause mixing of fluid in the analysis chamber, a reagent section containing a reagent composition, and a passage extending between the agitator section and the reagent section, passage adapted to permit fluid flow between the agitator section and the reagent section at both ends of the agitator section in response to movement of the agitator, wherein the fluid passage is an axial slot narrower than a minimum dimension of the agitator so that the agitator cannot pass into the reagent chamber;
at least one reference chamber in the housing, the reference chamber not including a magnetically movable element;
a distribution gallery in the housing and located radially inward from and fluidly connected to the analysis chambers, the distribution gallery adapted to distribute a liquid to be analyzed to the analysis chambers through centrifugal force upon rotation of the cartridge about the axis; and
a fluid port in the housing and fluidly connected to the distribution galley; the fluid port adapted to permit a fluid to be dispensed into the housing.

14. The analytical cartridge of claim 13, wherein the fluid port is located at one end of the distribution gallery, and wherein an overflow chamber is connected at another end of the galley; and wherein the fluid connection with the analysis chambers includes a plurality of channels located between the fluid port and the overflow chamber, the channels extending radially from the distribution gallery, each channel connected to an analysis chamber.

15. The analytical cartridge of claim 13 wherein the analysis chambers and the at least one reference chamber are evenly spaced circumferentially about the axis, and wherein the overflow chamber is larger than one of the analysis chambers, and the overflow chamber and the at least one reference chamber together occupy the same space as two analysis chambers.

16. The analytical cartridge of claim 13, wherein the agitator is a ball bearing.

* * * * *